(12) United States Patent
Cullen

(10) Patent No.: US 11,134,903 B2
(45) Date of Patent: Oct. 5, 2021

(54) DIGITAL DENTAL X-RAY SENSOR DEVICE HAVING A ROUNDED HOUSING

(71) Applicant: Shayda Cullen, Tampa, FL (US)

(72) Inventor: Shayda Cullen, Tampa, FL (US)

(*) Notice: Subject to any disclaimer, the term of this patent is extended or adjusted under 35 U.S.C. 154(b) by 114 days.

(21) Appl. No.: 16/715,826

(22) Filed: Dec. 16, 2019

(65) Prior Publication Data

US 2020/0113531 A1 Apr. 16, 2020

Related U.S. Application Data

(63) Continuation-in-part of application No. 16/162,080, filed on Oct. 16, 2018, now Pat. No. 10,506,992.

(51) Int. Cl.
*A61B 6/00* (2006.01)
*A61B 6/14* (2006.01)

(52) U.S. Cl.
CPC ............... *A61B 6/145* (2013.01); *A61B 6/14* (2013.01); *A61B 6/42* (2013.01); *A61B 6/4208* (2013.01); *A61B 6/4283* (2013.01); *A61B 2562/164* (2013.01)

(58) Field of Classification Search
CPC .. A61B 6/14; A61B 6/145; A61B 6/42; A61B 6/4208; A61B 6/4283
USPC ....................... 378/98.8, 168–170, 189, 191; 250/370.09
See application file for complete search history.

(56) References Cited

U.S. PATENT DOCUMENTS

| | | | | |
|---|---|---|---|---|
| 4,912,740 A * | 3/1990 | Liese, Jr. | ............... | B29C 70/763 378/169 |
| 5,331,166 A * | 7/1994 | Crosetto | .................. | H05G 1/44 250/370.11 |
| 5,677,537 A * | 10/1997 | Pfeiffer | ..................... | A61B 1/05 250/370.09 |
| 5,691,539 A * | 11/1997 | Pfeiffer | .................. | A61B 6/145 250/370.09 |
| 6,169,781 B1 * | 1/2001 | Doebert | ................. | A61B 6/145 378/189 |
| 6,320,934 B1 * | 11/2001 | Carroll | ..................... | A61B 6/14 348/E3.02 |
| 6,652,141 B1 * | 11/2003 | Cianciosi | ............... | A61B 6/145 378/191 |
| 6,811,312 B2 * | 11/2004 | Bratslavsky | ......... | G03B 42/042 378/191 |
| 7,210,847 B2 * | 5/2007 | Hack | ....................... | A61B 6/145 206/455 |
| 7,281,847 B2 * | 10/2007 | Kokkaliaris | ........... | A61B 6/145 348/E5.026 |
| 7,891,871 B2 * | 2/2011 | Ayraud | .................. | A61B 6/563 378/191 |
| 7,972,060 B2 * | 7/2011 | Guichard | ............... | A61B 6/145 378/191 |

(Continued)

*Primary Examiner* — Allen C. Ho
(74) *Attorney, Agent, or Firm* — The Concept Law Group, PA; Scott D. Smiley; Scott M. Garrett

(57) ABSTRACT

A digital dental x-ray sensor device includes a rounded, three dimensional housing that lacks corners, edges, or other relatively sharp features that are known to cause discomfort when used in a patient's mouth. The rounded housing can be spherical, ellipsoid, or any similar regular or irregular rounded shape, and can be formed by ensuring that all curves of the surface of the rounded housing have a minimum radius that is sufficient to prevent features that can dig into the soft tissue of the inside of a patient's mouth.

20 Claims, 20 Drawing Sheets

(56) References Cited

U.S. PATENT DOCUMENTS

| | | | | |
|---|---|---|---|---|
| 8,320,525 | B2* | 11/2012 | Khouri | A61B 6/4233 378/98.8 |
| 8,366,318 | B2* | 2/2013 | Zeller | H04N 5/23203 378/169 |
| 9,216,003 | B1* | 12/2015 | Chen | A61B 6/145 |
| 9,295,436 | B2* | 3/2016 | Nakao | A61B 6/145 |
| 9,314,215 | B2* | 4/2016 | Abramovich | G03B 42/042 |
| 9,351,692 | B2* | 5/2016 | Yao | A61B 6/4429 |
| 9,357,972 | B2* | 6/2016 | Chen | A61B 6/4233 |
| 9,498,170 | B2* | 11/2016 | Schwarzbach | A61B 6/145 |
| 9,636,071 | B2* | 5/2017 | Heo | A61B 6/425 |
| 9,801,593 | B2* | 10/2017 | Kravis | A61B 6/467 |
| 9,901,313 | B2* | 2/2018 | Schmulenson | G03B 42/042 |
| 9,907,521 | B2* | 3/2018 | Papaix | A61B 6/5205 |
| 9,907,530 | B2* | 3/2018 | Charnegie | A61B 6/4494 |
| 10,010,300 | B2* | 7/2018 | Yao | A61B 6/145 |
| 10,092,255 | B2* | 10/2018 | Heo | A61B 6/145 |
| 10,130,317 | B2* | 11/2018 | Miller | H01L 27/14663 |
| 10,165,990 | B2* | 1/2019 | Kim | A61B 6/145 |
| 10,506,992 | B1* | 12/2019 | Cullen | A61B 6/42 |

* cited by examiner

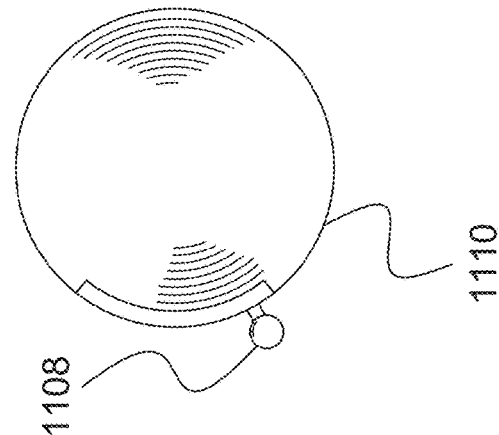
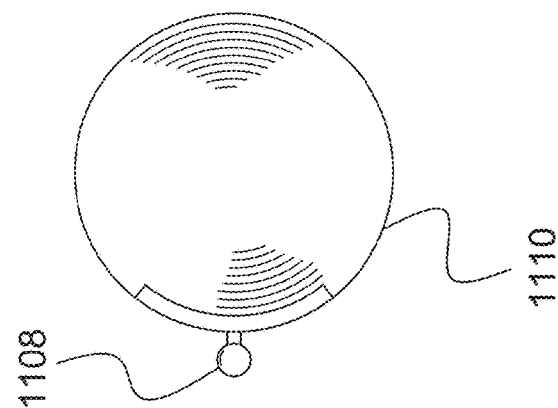
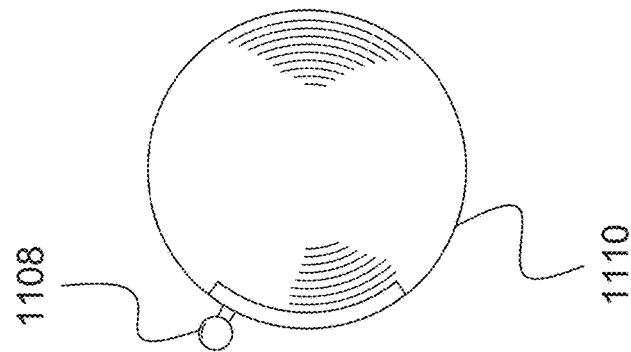
FIG.11

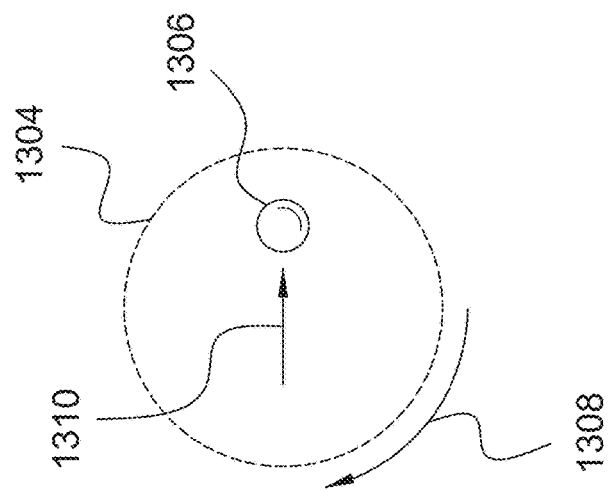
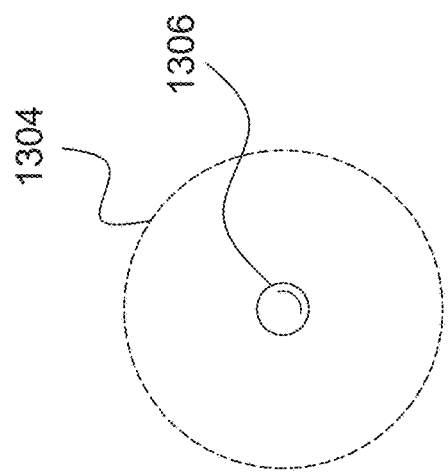
FIG.13

DIGITAL DENTAL X-RAY SENSOR DEVICE HAVING A ROUNDED HOUSING

CROSS REFERENCE

This application is a continuation in part of application Ser. No. 16/162,080, filed Oct. 16, 2018, now U.S. Pat. No. 10,506,992 issued on Dec. 17, 2019, the entirety of which is hereby incorporated by reference.

FIELD OF THE INVENTION

The present invention relates generally to dental x-ray sensors, and, more particularly, relates to a dental x-ray sensor device that fits comfortably in a person's mouth, and which allows broader angles of view to be taken by an x-ray compared to conventional x-ray sensors.

BACKGROUND OF THE INVENTION

Dentists have been using x-ray photography to examine teeth and dental work for decades. In the past a slide of film was placed in a protective rectangular sheath and put into a patient's mouth. These sheaths had uncomfortable edges and corners that contributed to the general unpleasantness associated with a visit to a dentist's office. Typically the corners and edges would dig into the patient's soft palate in the roof of their mouth, as well as in the lower jaw around the tongue. For some patients, particularly children, the shape of x-ray film sheaths made it very difficult to obtain good images. More recently, the film x-ray has been replaced by digital x-ray sensors. Digital x-ray sensors use conventional image sensor technology, such a complementary metallic oxide semiconductor (CMOS) image sensors, in combination with a scintillator that produces visible light in the presence of x-rays, to produce a digital image. However, these digital x-ray sensors have retained the conventional rectangular form factor, and most of the uncomfortableness associated with that form factor.

The rectangular cuboid/prism shape of conventional digital x-ray sensors can cause mild to extreme discomfort in some patients. Among the issues experienced by dental patients, people report that the x-ray sensor produces a "cutting" sensation on the inside of their mouth, the feeling of being "smothered," as well as inducing a gag reflex which can lead to vomiting. Different people have different sized mouths, so a large sensor for adults can still be difficult to accommodate by some adults with smaller mouths.

Therefore, a need exists to overcome the problems with the prior art as discussed above.

SUMMARY OF THE INVENTION

The invention provides a digital dental x-ray sensor device that overcomes the hereinafore-mentioned disadvantages of the heretofore-known devices and methods of this general type and that can be used comfortably by patients without the irritation and uncomfortableness associated with prior art dental x-ray sensors.

Embodiments of the inventive disclosure provide a dental x-ray sensor device that includes a rounded housing configured fit in a patient's mouth that is configured to contain a digital x-ray sensor having a front, the rounded housing having an external surface lacking edges or corners. The rounded housing can include a flat face that is circular or elliptical that corresponds to a plane of a digital x-ray sensor configured to be mounted in the rounded housing. The dental x-ray sensor device can further include a handle attachment feature formed on an outside surface of the rounded housing that is that is positioned to be in front of the digital x-ray sensor, and which allows attachment of a handle at a plurality of positions along the handle attachment feature.

In accordance with another feature, the rounded housing comprises a first and a second portion that are configured to separably couple together and which provide a sensor bed configured to receive a rectangular digital x-ray sensor.

In accordance with another feature, the rounded housing is semi-spherically shaped.

In accordance with another feature, the rounded housing is configured to contain a circular digital x-ray sensor that conforms to an internal cross section of the rounded housing, and wherein the dental x-ray sensor device further comprises the circular digital x-ray sensor.

In accordance with another feature, the handle attachment feature comprises a groove that is configured to receive a base of a coupling member having detent features, and wherein the groove has a plurality of corresponding detent features at positions along the groove.

In accordance with another feature, the rounded housing has an external surface having a minimum radius of five millimeters.

In accordance with another feature, the rounded housing comprises an indicia that indicates an orientation of the digital x-ray sensor inside the rounded housing.

In accordance with some aspects of the inventive disclosure, some embodiments can provide a digital dental x-ray sensor device including a rounded housing having an external surface that lacks edges and corners and that is configured to fit with a person's mouth with the person's mouth substantially closed. The rounded housing comprises a flat face that is circular or elliptical that corresponds to a plane of a digital x-ray sensor configured to be mounted in the rounded housing. The device can further include a digital x-ray sensor disposed within the rounded housing that conforms to an internal cross section of the rounded housing. The device can also include an attachment feature on an exterior of the rounded housing that is configured to receive a coupling member in a channel of the attachment feature.

In accordance with another feature, the rounded housing is a semi-spherical housing.

In accordance with another feature, the semi-spherical housing includes a shoulder.

In accordance with another feature, the rounded housing is an ellipsoid.

In accordance with another feature, the rounded housing comprises at least one flat spot.

In accordance with another feature, the digital x-ray sensor has a circular shape.

In accordance with another feature, the attachment feature is positioned on the rounded housing in front of the digital x-ray sensor.

In accordance with another feature, the attachment features comprises a plurality of detent features, each one of the plurality of detent features corresponding to a respective position along the channel and configured to mate with a corresponding detent feature on the coupling member.

In still some other embodiments of the inventive disclosure, there is provided a digital dental x-ray sensor system that includes a digital dental x-ray sensor device having a rounded housing, a digital x-ray sensor disposed within the rounded housing, and an attachment feature formed on an exterior of the rounded housing. The rounded housing comprises a flat face that is circular or elliptical that corresponds to a plane of a digital x-ray sensor configured to be mounted in the rounded housing. The system can further include a coupling member having a portion configured to fit within a channel of the attachment feature and be moveably retained in the channel, and having a head portion connected to the portion configured to fit within the channel. The system can further include a handle member having a first end configured to attach to the head of the coupling member, and having a second end opposite the first end. The system can further include a coupling ring configured to be retained on an emitter portion of an x-ray source, and having an extension that extends from a track formed on the coupling ring that is configured to attach to the second end of the handle member.

In accordance with another feature, the rounded housing is semi-spherical.

In accordance with another feature, the digital x-ray sensor is circular.

In accordance with another feature, the channel of the attachment feature comprises a plurality of detent features, where each one of the detent features is corresponds to a respective one of a plurality of positions along the channel, and the portion of the coupling member is configured to fit with the channel includes corresponding detent features to mate with the plurality of detent features in the channel to hold the coupling member at one of the plurality of positions along the channel.

In accordance with another feature, the extension of the coupling ring is movable along the track to hold the extension at a selected position along the track.

Although the invention is illustrated and described herein as embodied in a digital dental x-ray sensor and system, it is, nevertheless, not intended to be limited to the details shown because various modifications and structural changes may be made therein without departing from the spirit of the invention and within the scope and range of equivalents of the claims. Additionally, well-known elements of exemplary embodiments of the invention will not be described in detail or will be omitted so as not to obscure the relevant details of the invention.

Other features that are considered as characteristic for the invention are set forth in the appended claims. As required, detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one of ordinary skill in the art to variously employ the present invention in virtually any appropriately detailed structure. Further, the terms and phrases used herein are not intended to be limiting; but rather, to provide an understandable description of the invention. While the specification concludes with claims defining the features of the invention that are regarded as novel, it is believed that the invention will be better understood from a consideration of the following description in conjunction with the drawing figures, in which like reference numerals are carried forward. The figures of the drawings are not drawn to scale.

Before the present invention is disclosed and described, it is to be understood that the terminology used herein is for the purpose of describing particular embodiments only and is not intended to be limiting. The terms "a" or "an," as used herein, are defined as one or more than one. The term "plurality," as used herein, is defined as two or more than two. The term "another," as used herein, is defined as at least a second or more. The terms "including" and/or "having," as used herein, are defined as comprising (i.e., open language). The term "coupled," as used herein, is defined as connected, although not necessarily directly, and not necessarily mechanically. The term "providing" is defined herein in its broadest sense, e.g., bringing/coming into physical existence, making available, and/or supplying to someone or something, in whole or in multiple parts at once or over a period of time.

"In the description of the embodiments of the present invention, unless otherwise specified, azimuth or positional relationships indicated by terms such as "up", "down", "left", "right", "inside", "outside", "front", "back", "head", "tail" and so on, are azimuth or positional relationships based on the drawings, which are only to facilitate description of the embodiments of the present invention and simplify the description, but not to indicate or imply that the devices or components must have a specific azimuth, or be constructed or operated in the specific azimuth, which thus cannot be understood as a limitation to the embodiments of the present invention. Furthermore, terms such as "first", "second", "third" and so on are only used for descriptive purposes, and cannot be construed as indicating or implying relative importance.

As defined herein, the term "corner" refers to a point location on a surface where two or more planes of the surface meet. The term "edge" refers to a continuous line or curve along the meeting of two planes or faces of a surface. Furthermore, an edge can be rounded, having a radius of curvature of less than five millimeters and generally where two planes or faces of a surface meet at an angle of more than forty five degrees.

In the description of the embodiments of the present invention, it should be noted that, unless otherwise clearly defined and limited, terms such as "installed", "coupled", "connected" should be broadly interpreted, for example, it may be fixedly connected, or may be detachably connected, or integrally connected; it may be mechanically connected, or may be electrically connected; it may be directly connected, or may be indirectly connected via an intermediate medium. As used herein, the terms "about" or "approximately" apply to all numeric values, whether or not explicitly indicated. These terms generally refer to a range of numbers that one of skill in the art would consider equivalent to the recited values (i.e., having the same function or result). In many instances these terms may include numbers that are rounded to the nearest significant figure. Those skilled in the art can understand the specific meanings of the above-mentioned terms in the embodiments of the present invention according to the specific circumstances. Furthermore, it will be appreciated by those skilled in the art that the features of the various embodiments shown in the various drawings can be combined among the embodiments shown in the drawings.

BRIEF DESCRIPTION OF THE DRAWINGS

The accompanying figures, where like reference numerals refer to identical or functionally similar elements throughout the separate views and which together with the detailed description below are incorporated in and form part of the specification, serve to further illustrate various embodiments and explain various principles and advantages all in accordance with the present invention.

FIG. 11 a series of views from the side of a digital x-ray sensor device illustrating how a coupling member can be moved to different positions in the attachment feature of the digital x-ray sensor device, in accordance with some embodiments;

FIG. 13 shows a front projection view of a coupling member is different positions relative to a digital x-ray sensor, in accordance with some embodiments;

DETAILED DESCRIPTION

Figure 1:
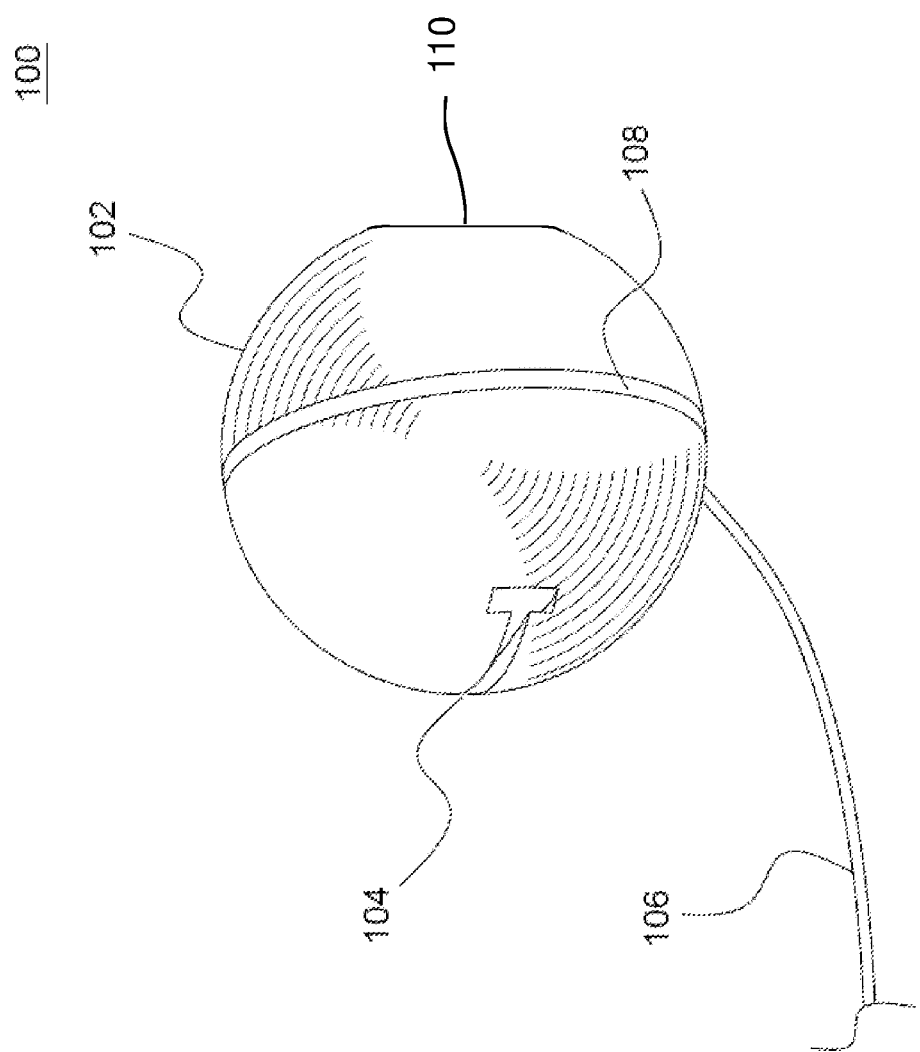
FIG. 1 is a digital x-ray sensor device having a rounded housing, in accordance with some embodiments.

While the specification concludes with claims defining the features of the invention that are regarded as novel, it is believed that the invention will be better understood from a consideration of the following description in conjunction with the drawing figures, in which like reference numerals are carried forward. It is to be understood that the disclosed embodiments are merely exemplary of the invention, which can be embodied in various forms.

Embodiments of the present inventive disclosure provide a novel and efficient digital dental x-ray sensor device that is configured to alleviate the problems associated with conventional digital dental x-ray sensors. In particular, embodiments provide a rounded housing that has no corners, points, or edges that would cause pain in the soft tissue of a patient's mouth. Furthermore, the rounded housing reduces triggering a gag reflex in some patients who may otherwise be susceptible to gagging when using conventional digital dental x-ray sensors. In addition, the inventive disclosure provides features for adjusting the attachment location of the digital x-ray sensor device to a handle that can be connected to an x-ray source in order to optimize the position of the digital x-ray sensor in the patient's mouth for a given x-ray image.

FIG. 1 is a digital x-ray sensor device 100 having a rounded housing 102, in accordance with some embodiments. The digital x-ray sensor device 100 is a device used to produce dental x-ray images while avoiding the problems associated with conventional, rectangular x-ray sensors. The digital x-ray sensor device 100 is used by placing it in the mouth of a patient, orienting it properly, and directing a beam of x-ray emissions towards the digital x-ray sensor device 100. The digital x-ray sensor device 100 produces a digital image of the patient's teeth, gums, and supporting bone in response to the x-ray emissions.

Many patients have experienced discomfort in using conventional rectangular prismatic dental x-ray sensors due to the corners and edges of these conventional sensors, which can result in discomfort ranging from mild pain to inducing a gag response or even vomiting. To reduce the discomfort experienced by patients, the digital x-ray sensor device 100 includes a rounded housing 102, meaning the external surface of the rounded housing 102 is rounded, and lacks corners, protrusions, or edges that could dig into the patient's soft tissue, particularly at the top and bottom of the rounded housing 102. Furthermore, the rounded housing 102 lacks any regions where two planar faces meet to form an edge. In some embodiments the rounded body can include one or more isolated planar faces 110 having a perimeter that meets rounded surfaces (e.g. a flat spot). In some embodiments, the rounded housing 102 can be spherical in shape, although not necessarily a perfect sphere. The rounded housing 102 can be an eccentric or irregular spheroid or ellipsoid (e.g. egg-shaped), having a width or length that is longer or shorter than dimensions in other directions, or it can include external surface feature such as bulges or depressions in some places. In some embodiments the rounded housing can have a flattened face on the external surface that is aligned (e.g. parallel) to a plane of an x-ray image sensor inside the digital x-ray sensor device 100. In some embodiments the rounded housing 102 can have a flat spot to prevent the digital x-ray sensor device 100 from rolling when not in use and sitting on a surface. Although the rounded housing 102 can occupy more volume in a patient's mouth than a conventional rectangular prism shaped sensor, the rounded housing 102 eliminates any features that could dig into, or otherwise contact, the patient's soft tissue inside the patient's mouth, and cause the type of discomfort associated with the conventional x-ray sensor form factors. In some embodiments the rounded housing can have features with convex curves having a radius of not less than five millimeters over the majority of the external surface of the rounded housing. Some features may be present in locations that will not be against the patient's soft tissue in their mouth that have a smaller curve radius.

The rounded housing 102 is provided with an attachment feature 104 to allow the rounded housing 102 to couple to a handle or support member that is used to properly align the digital x-ray sensor device 100 in the patient's mouth. A cable 106 is connected to the internal circuitry of the digital x-ray sensor device 100 and allows transmission of instruction and information to and from the digital x-ray sensor device 100, including the transmission of image data from the digital x-ray sensor device 100 to an image rendering computer system. An external indicia 108, such as a line or other indicia, can further be provided on an outside of the rounded housing 102 to indicate an orientation of the digital x-ray sensor device 100, and specifically an orientation of the image sensor housing inside the rounded housing 102 to allow the technician or clinician to properly orient the digital x-ray sensor device 100 device with respect to the particular teeth being x-rayed. In some embodiments the attachment feature can be located in front of the internal image sensor housing within the rounded housing 102, meaning the attachment feature 104 will be between the x-ray source and the internal image sensor.

The attachment feature 104 can be a groove or channel formed in the surface of the rounded housing 102 that is configured to receive a coupling member which has a portion that fits within, and is retained by, the groove or channel. The attachment feature 104 can include structure that allows the coupling member to be positioned at various locations in the attachment feature 104 to achieve slightly different orientations of the digital x-ray sensor device 100 relative to the patient's teeth and an x-ray emitter located outside the patient. Thus, the attachment feature 104 can be used to optimally align and position the digital x-ray sensor device 100 to produce x-ray images of particular desired views of the patient's dental environment.

Figure 2:
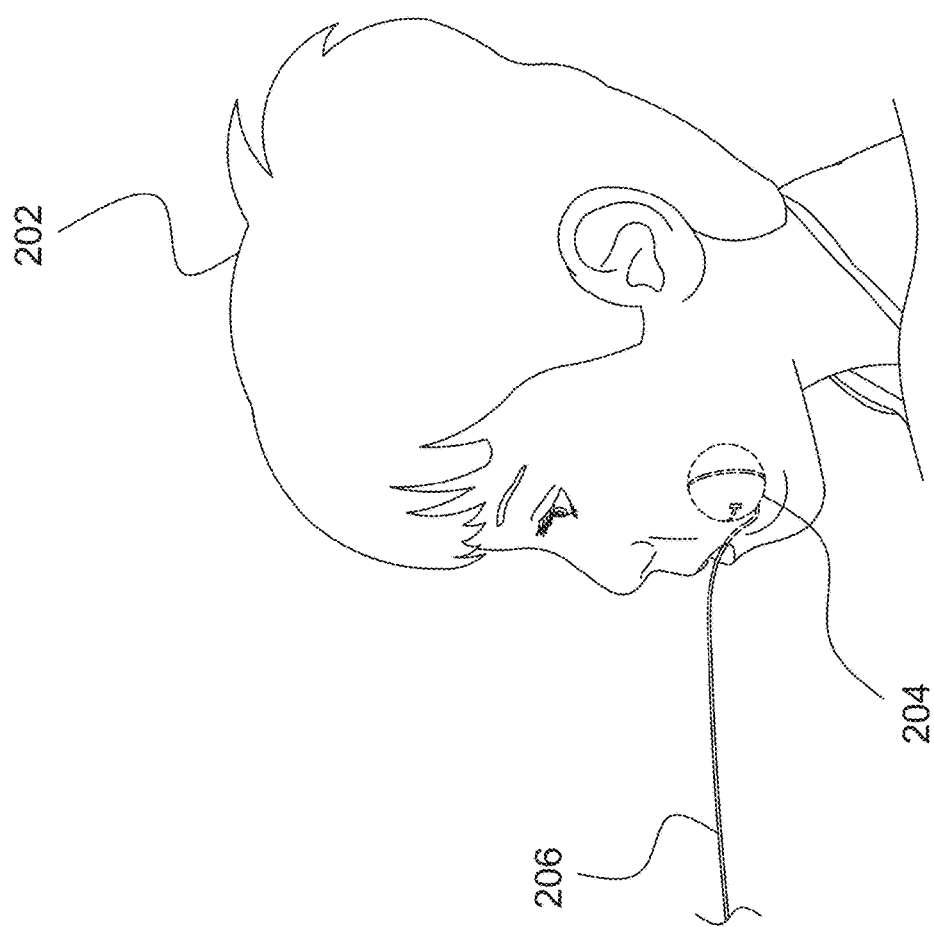
FIG. 2 is a side view of a patient having a dental x-ray taken while using a digital x-ray sensor device, in accordance with some embodiments.

FIG. 2 is a side view 200 of a patient 202 having a dental x-ray taken while using a digital x-ray sensor device 204, in accordance with some embodiments. The digital x-ray sensor device 204 is hidden from view as being inside the mouth of the patient 202, so the digital x-ray sensor device 204 is represented here in broken line. The digital x-ray sensor device 204 can be substantially similar to the digital x-ray sensor device 100 of FIG. 1. A technician can place the digital x-ray sensor device 204 in the mouth of the patient 202 in a proper orientation in cooperation with an external x-ray emitter source (not shown), as is known. The data cable 206 connected to the digital x-ray sensor device 204 passes out of the mouth of the patient 202 to an image rendering system.

Figure 3:
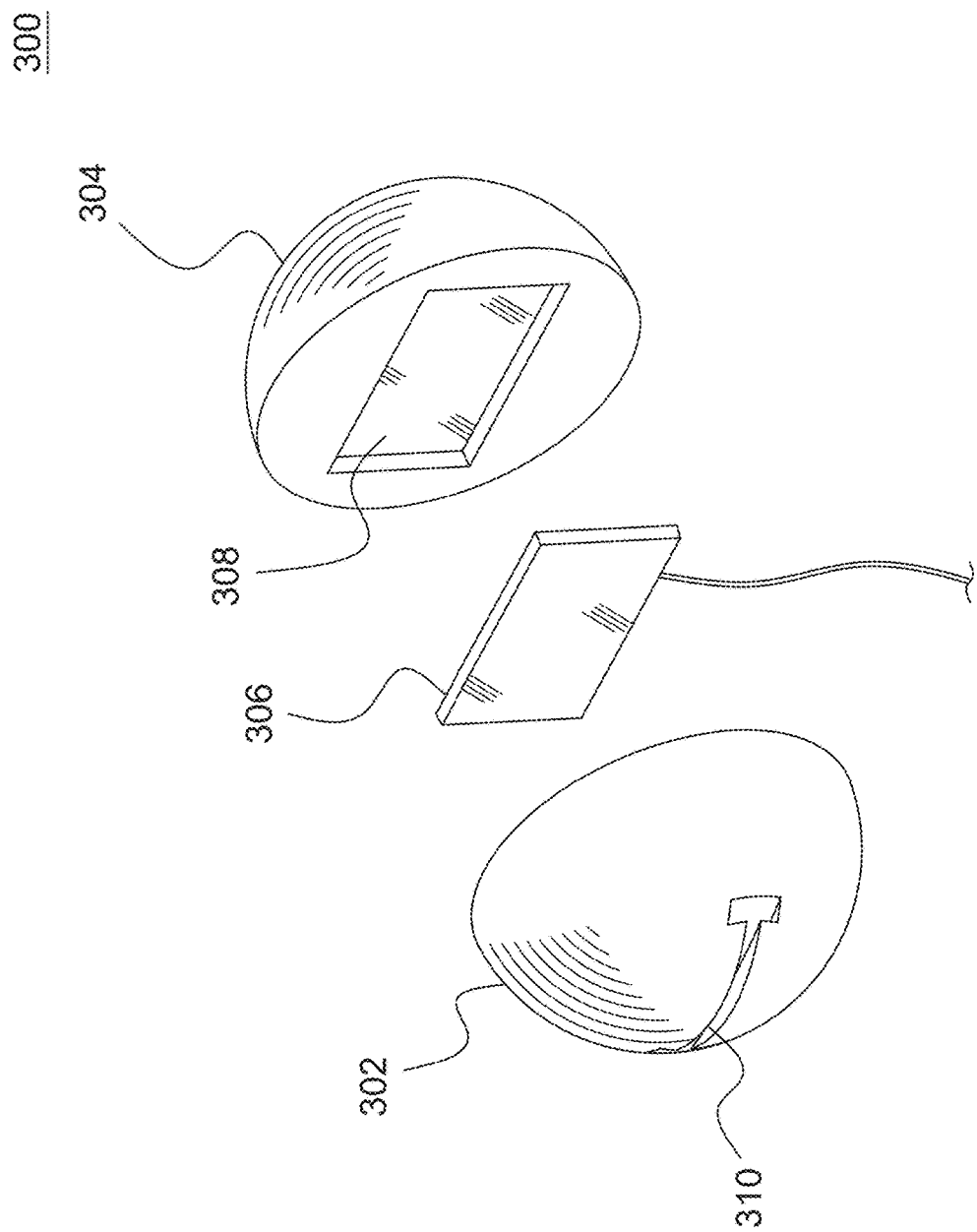
FIG. 3 is an exploded perspective view of a digital x-ray sensor device having a rounded housing for containing a conventional digital x-ray sensor, in accordance with some embodiments.

FIG. 3 is an exploded perspective view of a digital x-ray sensor device 300 having a rounded housing for containing a conventional rectangular digital x-ray sensor 306, in accordance with some embodiments. The housing can be comprised of two halves, such as a first half 302 and a second half 304. The housing portions 302, 304 can produce a sphere, ellipsoid, irregular sphere or ellipsoid, or other rounded shapes. The conventional rectangular digital x-ray sensor 306 can be held inside the housing portions 302, 304 in a bed 308 that is a physical arrangement that supports and holds the rectangular digital x-ray sensor 306 in place. In some embodiments, the bed 308 can include different bedding orientations to hold rectangular sensors of different sizes. The housing portions 302, 304 can couple together in a way that they are held together (e.g. with retention features) but which allow a technician to take them apart for cleaning, and use with other rectangular x-ray sensors. As in FIG. 1, the housing portions 302, 304 can include an attachment feature 310 on an external surface that allows coupling to a handle member. The conventional digital x-ray sensor 306 can be, for example, the type that is presently in use, including a polymeric external housing, or it can be a specially adapted housing including all of the sensor components and circuitry that could be used in conventional applications with a conventional housing.

Figure 4:
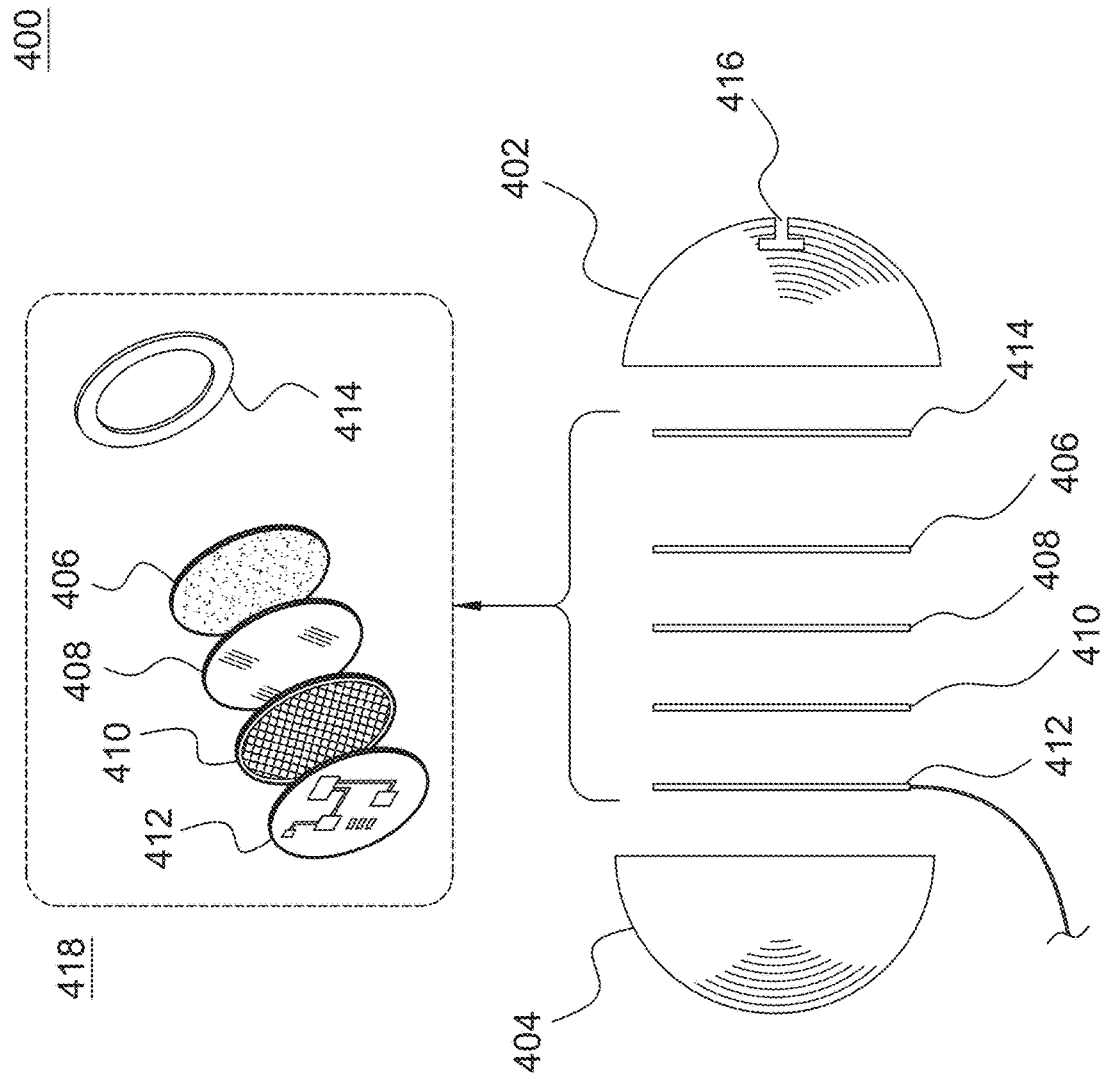
FIG. 4 is a side elevational exploded view of a digital x-ray sensor device having a rounded housing for containing a round digital x-ray sensor, in accordance with some embodiments.

FIG. 4 is a side elevational exploded view of a digital x-ray sensor device 400 having a rounded housing for containing a circular digital x-ray sensor, in accordance with some embodiments. The rounded housing can be comprised of housing portions 402, 404 which provide a rounded external surface in the shape of a sphere or other rounded surface, as described in reference to FIG. 1. The housing portions 402, 404 can be permanently, semi-permanently, or removably joined together, and provide an attachment feature 416. The housing portions 402, 404 house a digital x-ray sensor comprised of a stack of components that includes a scintillator 406, a fiber optic lensing array 408, a digital image sensor 410, and a circuit board 412. In some embodiments an annular shock pad 414, made of a compressible resilient material, can be provided as well to absorb mechanical shock experienced by the assembled device 400 to protect the other sensor components 406-412, which are shown in a perspective view detail 418.

The scintillator 406 is reactive to x-ray emissions and produces visible light in response, and in proportion to the intensity of the x-rays incident on the scintillator 406. Light produced by the scintillator 406 is directed through a fiber optic lensing array 408 to an image sensor 410. The lensing array 408 is comprised of segments of optical fiber placed in parallel in the plane of the lensing array 408 to direct light from the scintillator 406 to the image sensor 410, and to prevent bleeding of light from one portion of the scintillator 406 to adjacent portions of the image sensor 410. The image sensor can be a CMOS image sensor that converts light intensity to a digital value corresponding to the light intensity at each of a plurality of pixel locations, as is known. The circuit board 412 includes control and power circuity to drive and operate the image sensor 410, and further includes data communication circuity to transmit image data to a connected image rendering system (e.g. a computer).

The scintillator 406 is at the front of the stack, meaning it is closest to the x-ray source in use, and defines a front plane that is to be oriented in the direction of the x-ray source. Accordingly, the x-rays emitted from the x-ray source, when the digital x-ray sensor is correctly oriented for use, travel approximately perpendicular to the front plane of the scintillator 406.

In perspective detail 418, it can be seen that the sensor stack components 406-414 are substantially circular, or otherwise having a perimeter that conforms to the shape of the internal cross section space of the housing portions 402, 404. This arrangement reduces the unused area that remains when using a rectangular sensor, as in FIG. 4. With a substantially circular sensor configuration, the angle at which the digital x-ray sensor 400 is turned when placed in a patient's mouth is less relevant than with rectangular x-ray sensors.

Figure 5:
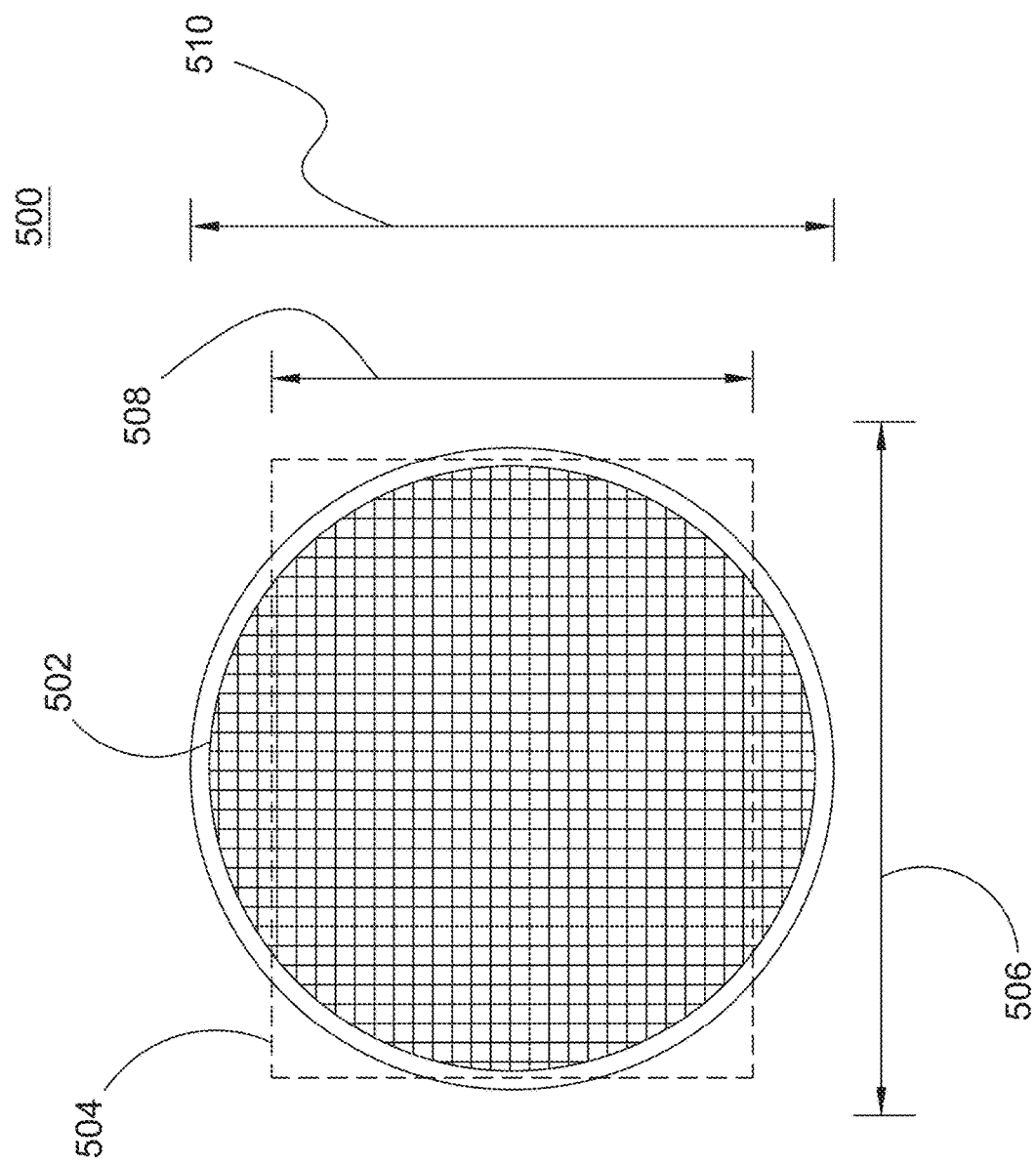
FIG. 5 is a front view of a round digital x-ray sensor, in accordance with some embodiments.

FIG. 5 is a front view 500 of a round digital x-ray sensor 502, in accordance with some embodiments. The round digital x-ray sensor 502 can be used in rounded digital x-ray sensor devices such as those shown in FIGS. 1 and 4. The x-ray sensor 500 can include all of the components 406-412 of FIG. 4. One advantage of the round/circular configuration is that the area of the circle maximizes the image area while also making it less crucial to have the top and bottom of the sensor aligned with the direction of the patient's teeth. For comparison, a rectangular x-ray sensor of a conventional size is projected over the circular x-ray sensor 502 in outline 504. The rectangular x-ray sensor projection 504 has a width dimension 506 that is equivalent to the diameter of the circular x-ray sensor 502, and a height dimension 508 that is only a portion of the height/diameter 510 of the circular x-ray sensor 502. However, the height 510 of the circular x-ray sensor 502 is also equal to its diameter, providing more image area above and below the rectangular projection, which can be regions of interest in dental x-rays. The corner regions of the rectangular projection 504 fall outside of the circular area of the circular x-ray sensor, but it is not typical to have image content of interest in these corner regions using conventional rectangular x-ray sensors.

Figure 6:
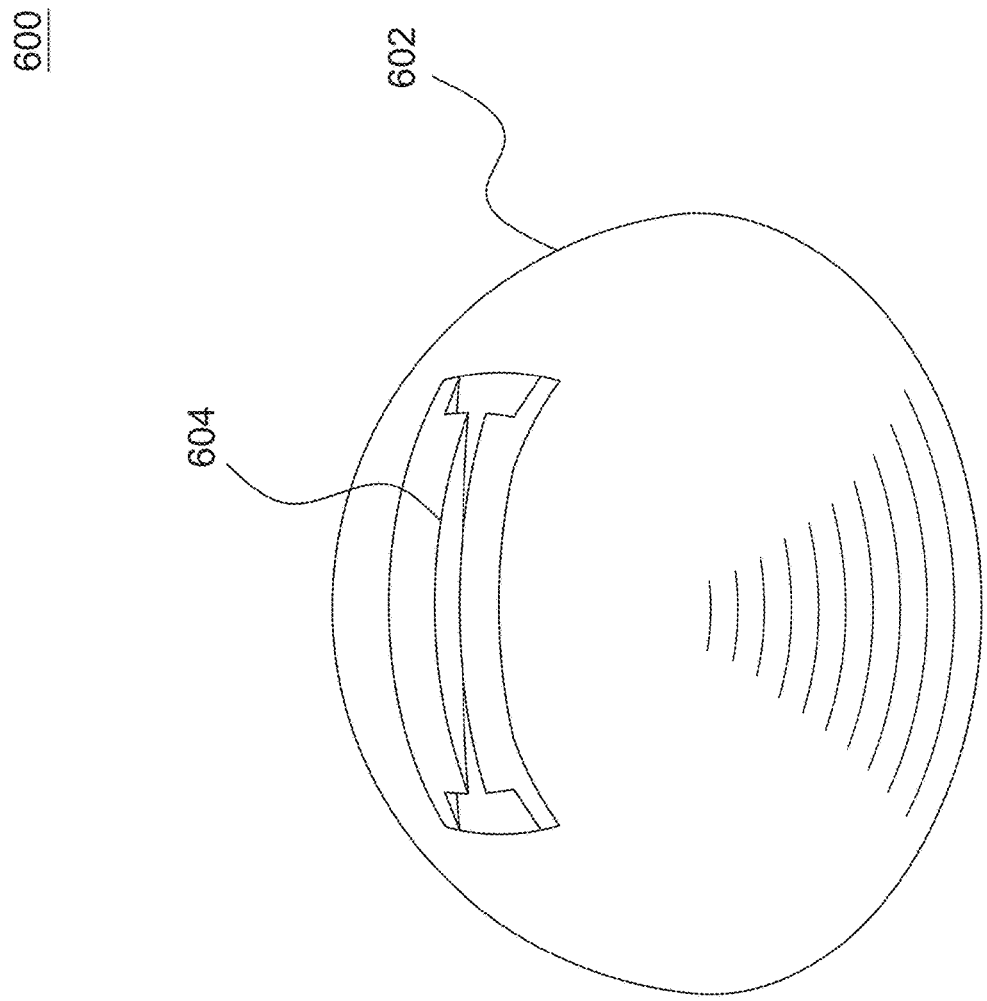
FIG. 6 is a side perspective view of a portion of a rounded housing of a digital x-ray sensor device with an attachment feature for coupling to a handle member, in accordance with some embodiments.
Figure 7:
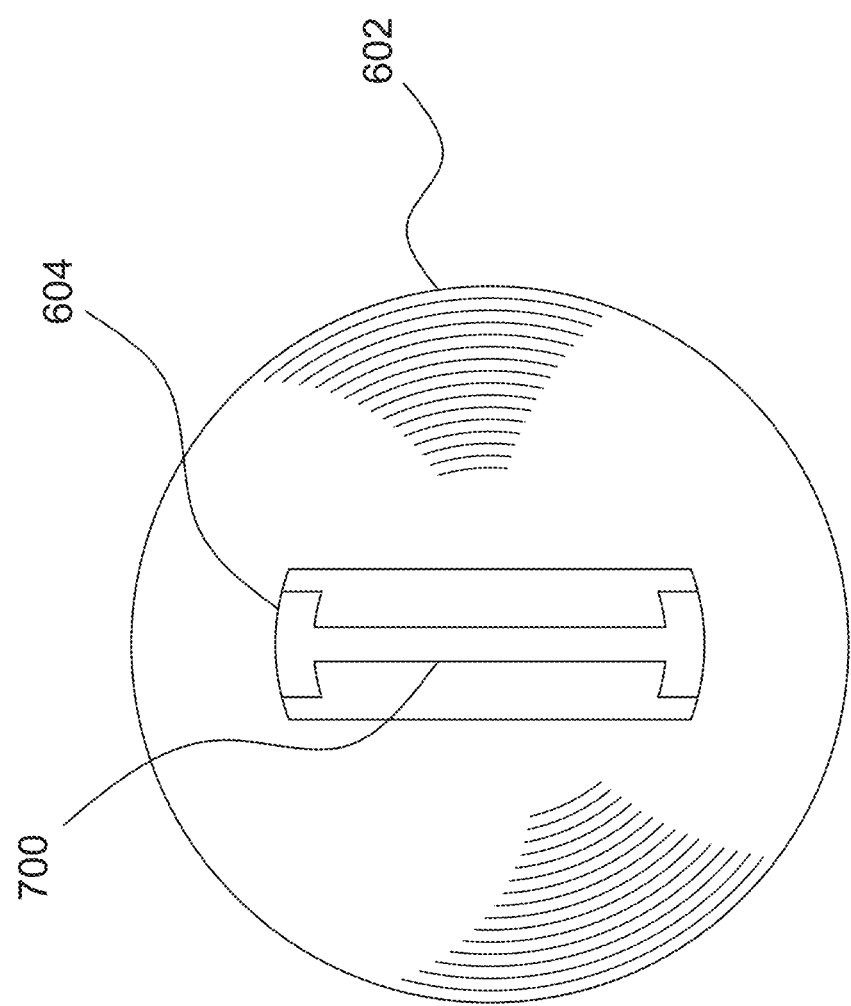
FIG. 7 is a front view of digital x-ray sensor device showing an attachment feature for coupling to a handle member, in accordance with some embodiments.
Figure 8:
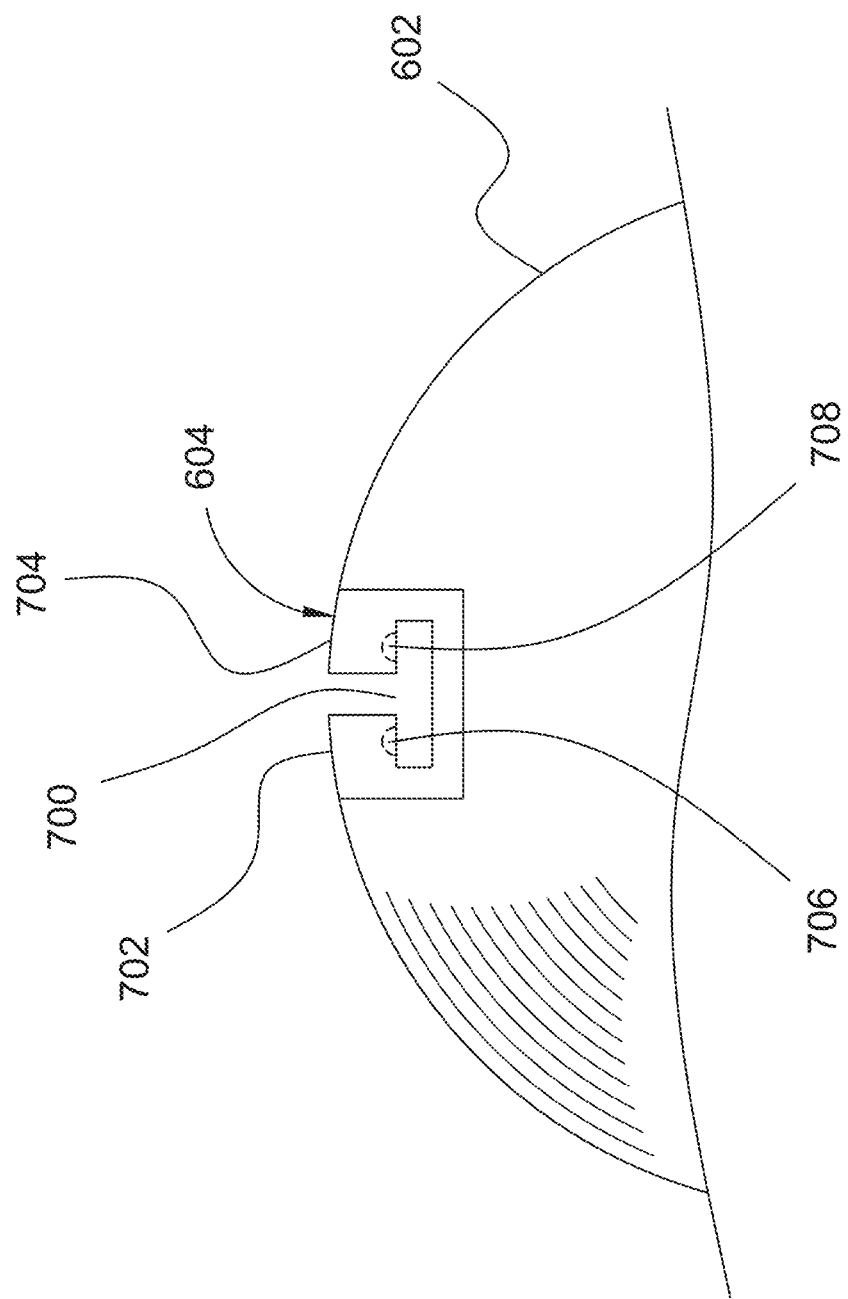
FIG. 8 is a side view of an attachment feature on the rounded housing of a digital x-ray sensor, in accordance with some embodiments.

FIGS. 6-8 show various view of a rounded housing for a digital x-ray sensor device, specifically showing detail of the attachment feature. FIG. 6 shows a side perspective view of a portion of a rounded housing of a digital x-ray sensor device; FIG. 7 shows a front view of digital x-ray sensor device; and FIG. 8 shows a side cut-away view of an attachment feature, looking along the channel of the attachment feature, on the rounded housing of a digital x-ray sensor.

A portion 600 of a rounded housing of a digital x-ray sensor includes an external surface 602 in which an attachment feature 604 is formed. As will be appreciated by those skilled in the art, there are numerous equivalent structures that can be used to couple a handle member to the rounded housing. In one example of an attachment feature 604, a channel or groove 700 is formed in the external surface 602. The channel 700 can include overhang or shoulder portions 702, 704 on either side of the channel 700 that capture a portion of a coupling member in the channel 700. The shoulder portions 702, 704 can have detent features 706, 708 at positions along the channel 700 to hold the coupling member at those positions, while also allowing the coupling member to be moved to different positions in the channel 700. The distance between the bottom of the shoulder portions 702, 704, in the channel 700, and the external surface of the housing 602 can be constant and follow the curve of the external surface over the shoulder portions 702, 704, or it can be straight through the housing, having a varying distance between the bottom of the shoulder portions 702, 704 and the external surface 602, However, the distance between the bottom of the shoulder portions 702, 704 and the bottom the channel 700 will be substantially constant along the channel to accommodate the base of the coupling member that is placed in the channel 700.

The detent features 706, 708 can be depressions formed in the bottom of the shoulder portions 702, 704 in some embodiments that correspond with complementary detent features in the coupling member. In some embodiments different detent features may be equivalently used. In some embodiments there can be detents corresponding to several positions along the channel 700 to accommodate different mouth shapes. For example, in some embodiments there can be five positions including a top, middle top, middle, middle bottom, and bottom. This allows the technician/clinician to adjust the position of the digital x-ray sensor device so that it sits comfortably in the patient's mouth while still being able to orient the digital x-ray sensor device to obtain the desired x-ray image.

Figure 9:
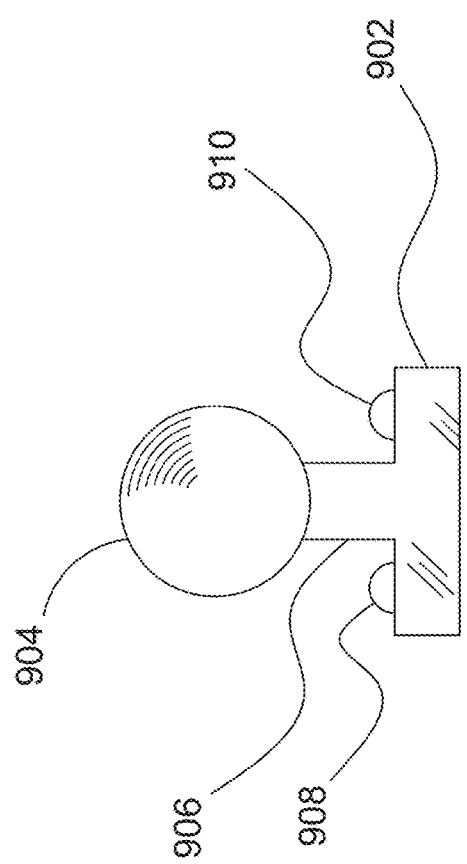
FIG. 9 shows a side view of a coupling member for coupling a handle member to an attachment feature of a digital x-ray sensor, in accordance with some embodiments.

FIG. 9 shows a side view of a coupling member 900 for coupling a handle member to an attachment feature of a digital x-ray sensor, in accordance with some embodiments. The coupling member 900 can be used in conjunction with the attachment feature of FIGS. 6-8, for example. The coupling member 900 includes a base portion 902 that is configured to be captured in channel 700, under shoulders 702, 704. A shaft portion 906 is configured to extend upwards from the base portion 902 between shoulders 702, 704, with detent features 908, 910 being configured to mate with detent features 706, 708. On top of the shaft portion is a ball-shaped head 904 that is configured to mate with a handle member is a ball and socket coupling arrangement.

Figure 10:
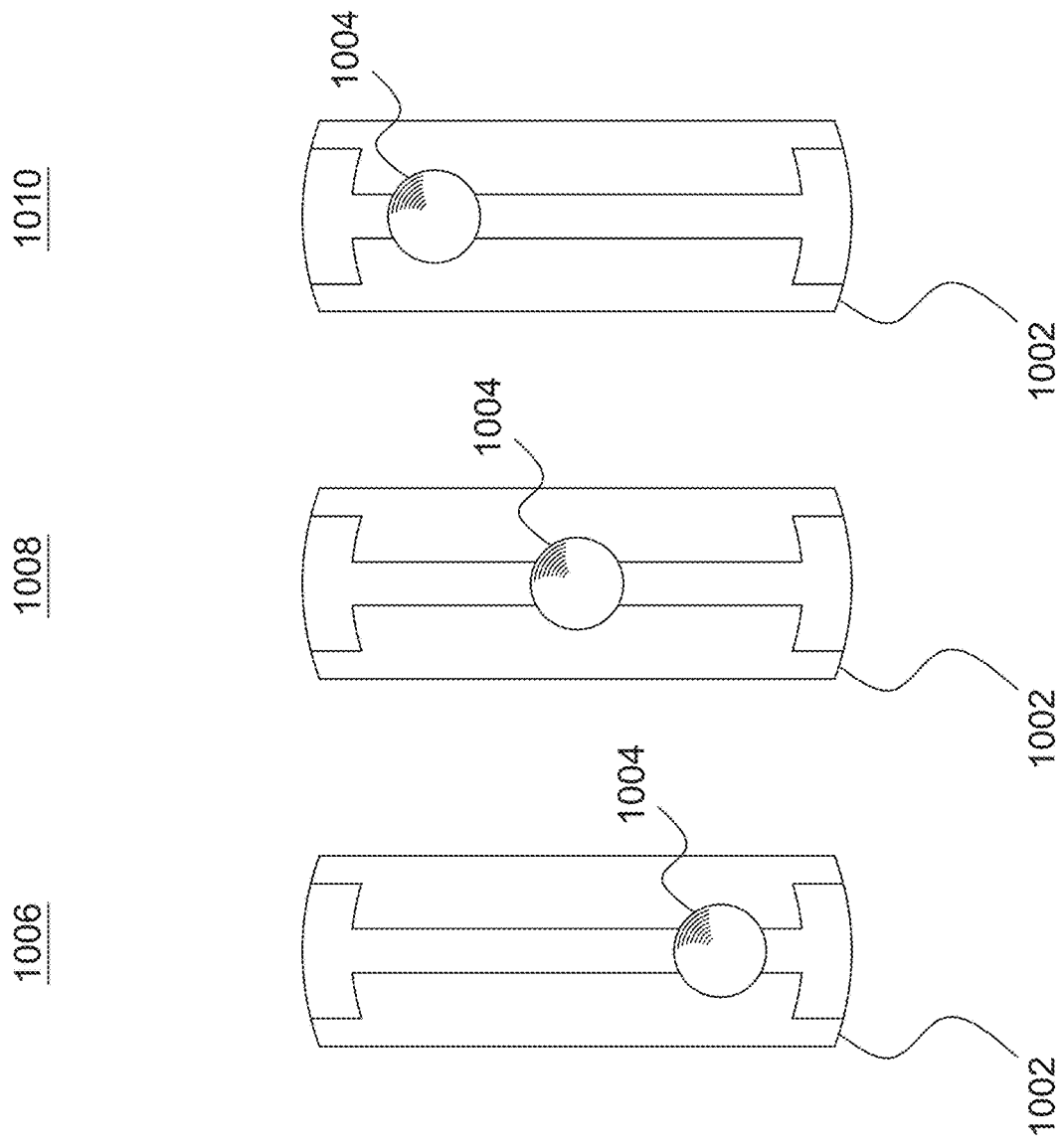
FIG. 10 shows a series of views from the front of a digital x-ray sensor device illustrating how a coupling member can be moved to different positions in the attachment feature of the digital x-ray sensor device, in accordance with some embodiments.

FIG. 10 shows a series of views from the front of a digital x-ray sensor device illustrating how a coupling member 1004 can be moved to different positions in the attachment feature 1002 of the digital x-ray sensor device, in accordance with some embodiments. The attachment feature 1002 is shown with a the head of a coupling member 1004 in three different exemplary positions 1006, 1008, 1010 which correspond to different detent locations. The attachment feature 1002 and the coupling member 1004 can be substantially similar to attachment feature 604 of FIGS. 6-8 and coupling member 900 of FIG. 9, respectively. Position 1006 shows the coupling member 1004 closer to a first end of the attachment feature 1002. Position 1008 shows the coupling member 1004 in the middle of the attachment feature 1002. Position 1010 shows the coupling member 1004 near a second end of the attachment feature 1002. A technician can select any of the available positions provided on an attachment feature to optimize the orientation and position of the digital x-ray sensor device in the patient's mouth for producing an x-ray image.

FIG. 11 a series of views 1102, 1104, 1106 from the side of a digital x-ray sensor device 1110 illustrating how a coupling member 1108 can be moved to different positions in the attachment feature of the digital x-ray sensor device, in accordance with some embodiments. The views 1102, 1104, 1106 can correspond to positions 1006, 1008, 1010, respectively, of FIG. 10. The digital x-ray sensor device 1110 includes a rounded housing, and can be designed substantially in accordance with the digital x-ray sensor device of FIG. 1, for example. FIG. 13 shows the effect of moving the coupling member to different locations in the attachment feature of the digital x-ray sensor device in two views 1300, 1302. In both views 1300, 1302 the front of a circular x-ray sensor 1304 (in broken line) is facing the outwards from the page, and the viewer's perspective is from approximately the location of an x-ray source that would be used with the digital x-ray sensor 1304. In view 1300 the coupling member 1306 is centered over the front of the circular x-ray sensor 1304, corresponding with 1008 and 1104 of FIGS. 10 and 11, respectively. In this position the circular image sensor 1304 is equally above and below the point where the patient's upper and lower teeth meet. In view 1302 the coupling member 1304 is moved to the side, as indicated by arrow 1310, resulting in a larger portion of the circular digital x-ray sensor being positioned to the left of the coupling member 1306. This position can be used, for example, when imaging the molar teeth of the patient. Thus, the attachment point, at the coupling member, can be used to adjust the position of the digital x-ray sensor in a given patient's mouth, for a particular x-ray image, and make it more comfortable for the patient.

Figure 12:
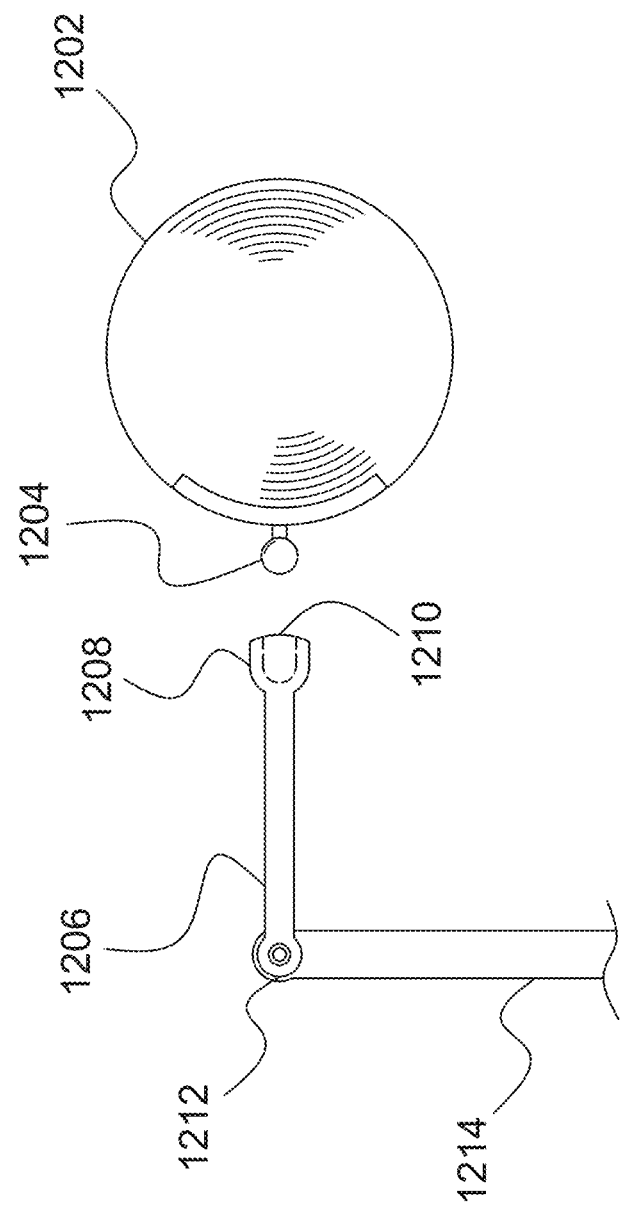
FIG. 12 shows a handle member that is configured to couple to the coupling member to couple to a digital sensor device, in accordance with some embodiments.

FIG. 12 shows a handle member 1206 that is configured to couple to the coupling member 1204 to couple to a digital x-ray sensor device 1202, in accordance with some embodiments. The handle member 1206 includes an engaging feature at an end 1208 for connecting to the coupling member 1204, such as a socket 1210 formed inside the end 1208 that is configured to retain the ball or head portion of the coupling member 1204 in the socket 1210. The socket 1201 is a hollow region in the material of the ends 1208 that can be a flexible resilient material, allowing the head of the coupling member 1204 to be inserted and removed from the socket 1210. The socket 1210 is formed such that its opening has a diameter that is slightly smaller than a diameter of the head of the coupling member 1204 to capture the head of the coupling member 1204 in the socket 1210, and allow for some movement/rotation of the head of the coupling member 1204 in the socket 1210. In some embodiments, the socket 1210 can include a slot cut on a side of the socket to allow the shaft on which the coupling member 1204 is located to pass into the slot, allowing for arm of the handle 1206 on which the socket is located to be positioned at a greater angle relative to the coupling member 1204. The portion of the handle 1206 including the socket 1210 can be joined to second portion 1214 at a hinge or joint 1212. The second portion 1214 can be coupled to an alignment structure that attaches to the x-ray source device to ensure that the x-ray source is positioned correctly with respect to the digital x-ray sensor.

Figure 20:
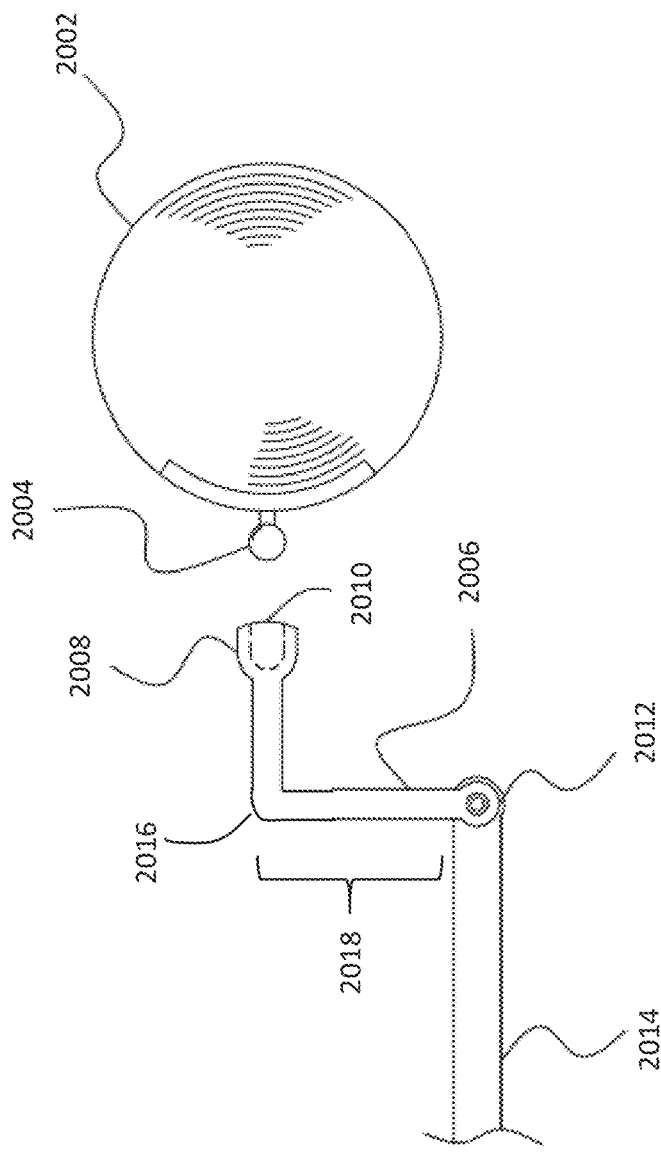
FIG. 20 shows a handle member that is configured to couple to the coupling member to couple to a digital sensor device, in accordance with some embodiments.

FIG. 20 shows a handle member 2006 that is configured to couple to the coupling member 2004 to couple to a digital x-ray sensor device 2002, in accordance with some embodiments, using an angled handle member 2006, that has a bend, such as at an elbow 2016. The elbow 2016 bends to create an offset 2018 form the second portion 2014. The offset 2018 can have a distance selected for a desired alignment of the digital x-ray sensor 2002 in a patient's mouth. As in the embodiment of FIG. 12, the handle member 2006 includes an engaging feature at an end 2008 for connecting to the coupling member 2004, such as a socket 2010 formed inside the end 2008 that is configured to retain the ball or head portion of the coupling member 2004 in the socket 2010. The socket 2010 is a hollow region in the material of the end 2008 that can be a flexible resilient material, allowing the head of the coupling member 2004 to be inserted and removed from the socket 2010. The socket 2010 is formed such that its opening has a diameter that is slightly smaller than a diameter of the head of the coupling member 2004 to capture the head of the coupling member 2004 in the socket 2010, and allow for some movement/ rotation of the head of the coupling member 2004 in the socket 2010. In some embodiments, the socket 2010 can include a slot cut on a side of the socket to allow the shaft on which the coupling member 2004 is located to pass into the slot, allowing for arm of the handle 2006 on which the socket is located to be positioned at a greater angle relative to the coupling member 2004. The portion of the handle 2006 including the socket 2010 can be joined to second portion 2014 at a hinge or joint 2012. The second portion 2014 can be coupled to an alignment structure that attaches to the x-ray source device to ensure that the x-ray source is positioned correctly with respect to the digital x-ray sensor.

Figure 14:
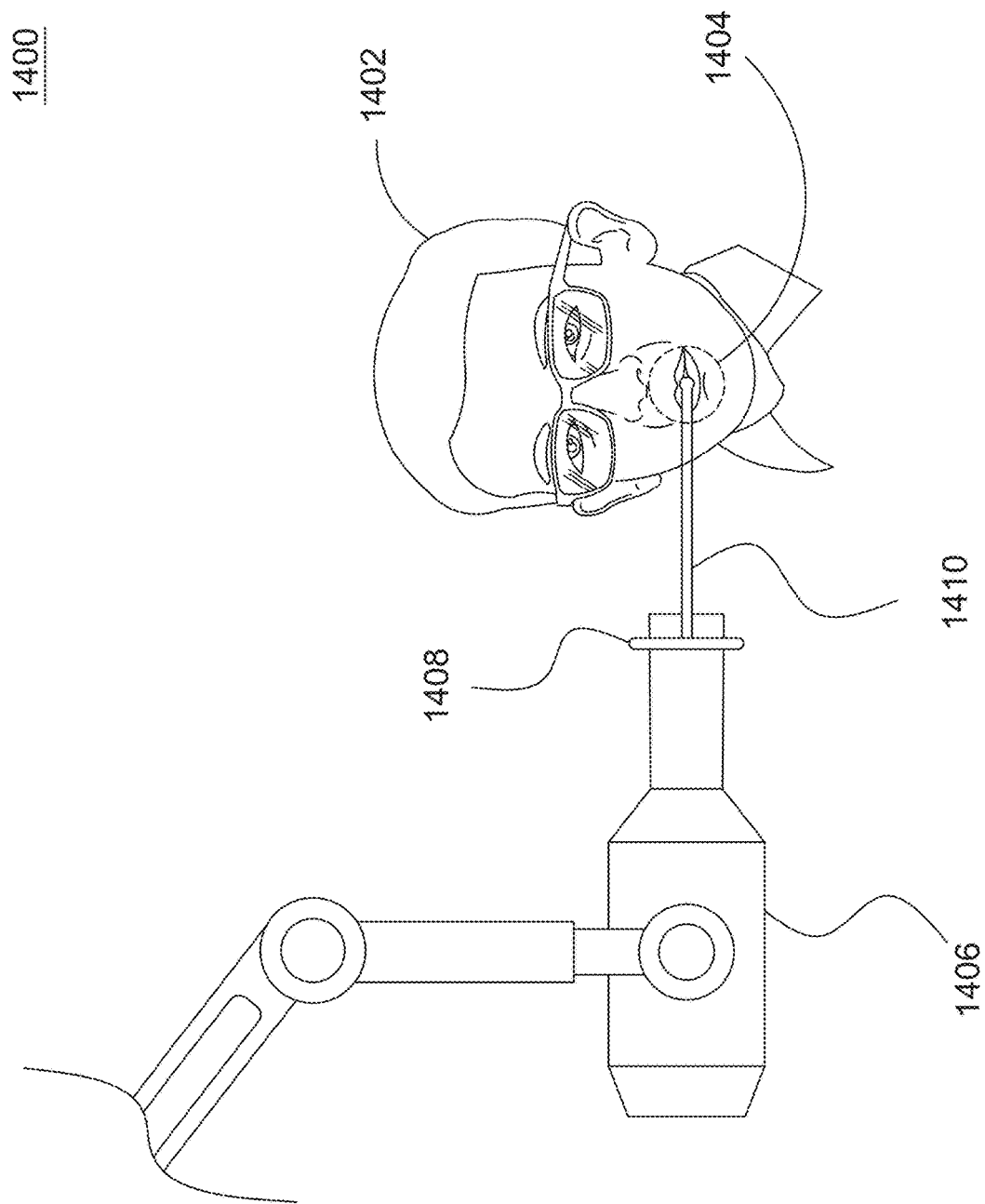
FIG. 14 shows a front view of a patient using a digital x-ray sensor, in accordance with some embodiments.

FIG. 14 shows a front view 1400 of a patient 1402 using a digital x-ray sensor 1404, in accordance with some embodiments, including a handle member 1410 coupled to an alignment structure 1408 that is further attached to the emitter of an x-ray source 1406. A handle member 1410 such as that shown in FIG. 12 can be coupled to a digital x-ray sensor 1404 that is placed in the mouth of the patient 1402. The handle member 1410, being further attached to the alignment structure 1408, which aligns the direction of the x-rays emitted by the x-ray source 1406 towards the x-ray sensor in the digital x-ray sensor 1404. The alignment structure 1408 can include a coupling ring that encircles the emitter housing, as is known.

Figure 15:
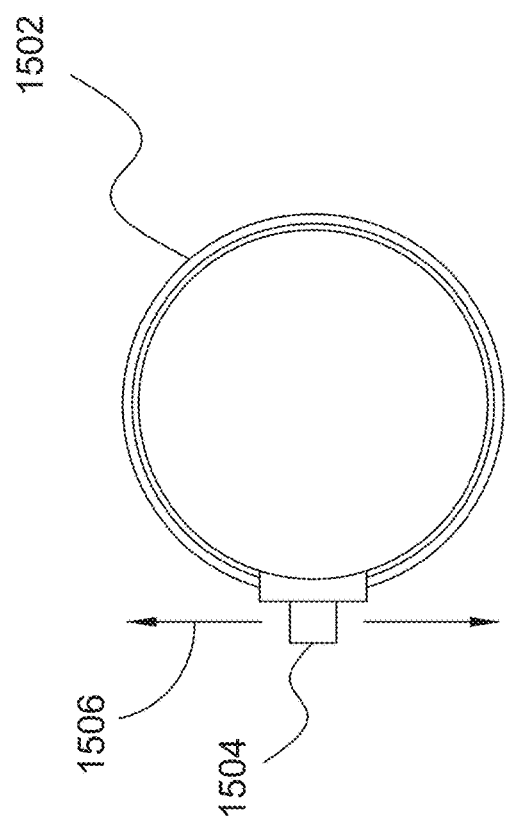
FIG. 15 shows a coupling ring for attaching a digital x-ray sensor to an x-ray source device, in accordance with some embodiments.

FIG. 15 shows a coupling ring 1500 for attaching a digital x-ray sensor to an x-ray source device, in accordance with some embodiments. The coupling ring 1502 is sized to go over the cylindrical emitter of an x-ray source, such as x-ray source 1406 of FIG. 14. The handle member attaches to an extension 1504 that extends outward from the coupling ring 1502 in a track that allows the extension 1504 to move in the track, as indicated by arrow 1506, for example. This allows the position of the attachment point of the handle to the coupling ring 1502 to be adjusted by the technician to allow optimum positioning of the x-ray source and the x-ray sensor device. In conventional devices, the coupling ring 1502 includes multiple, separate attachment points, which require the technician to remove the handle, and attach it to a different position when re-positioning the system for a different x-ray image. By providing the extension 1504 that is moveable in a track 1506 on the coupling ring 1502, the handle does not need to be disconnected from the coupling ring 1502 to reposition the handle with respect to the coupling ring 1502.

Figure 16:
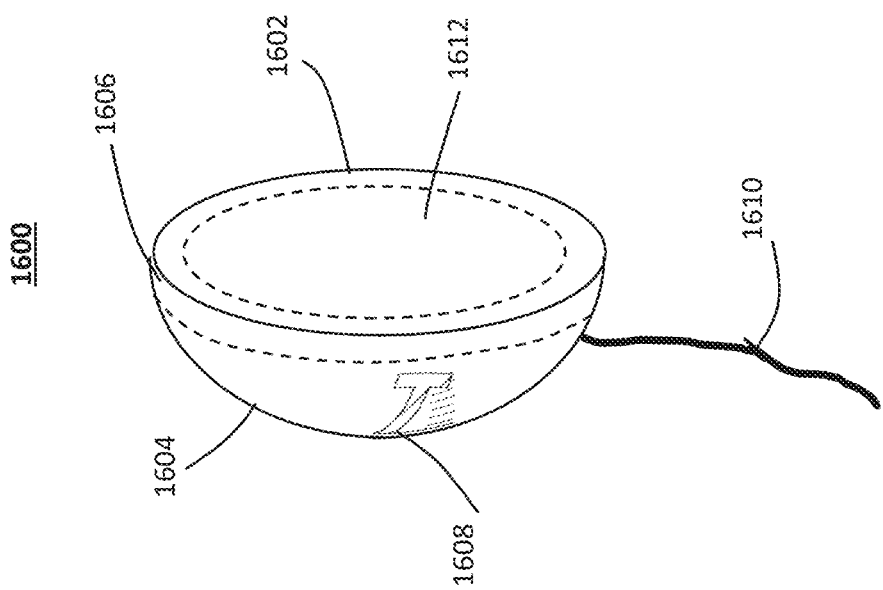
FIG. 16 shows a rounded housing of a digital x-ray sensor device in a semi-sphere configuration, in accordance with some embodiments.

FIG. 16 shows a rounded, semi-spherically configured housing 1600 of a digital x-ray sensor device in a semi-sphere configuration, in accordance with some embodiments. The semi-spherically configured housing 1600 includes a rounded, semi- or hemi-spherical portion 1602 and a flat surface 1602 that is a face formed along a plane through a sphere consistent with the semi-spherical portion 1604. That is, if the semi-spherical portion were extended to a full sphere, the flat surface 1602 passes through that sphere. The semi-spherically configured housing 1600 can further include a shoulder 1606 between the flat surface 1602 and the semi-spherical portion 1604 that extends around, or partially around the semi-spherically configured housing, adjacent to, and around the periphery of the flat surface. A handle attachment feature 1608 can be formed on an external portion of the semi-spherically configured housing, and a cable or wire assembly 1610 can connect to circuitry inside the semi-spherically configured housing 1600. The handle attachment feature 1608 can be formed substantially similar to the handle attachment features shown in FIGS. 6-12. In some embodiments a circular digital x-ray sensor 1612 can be housed inside the semi-spherically configured housing 1600, and the circular digital x-ray sensor 1612 can define a plane that is parallel with a plane of the flat surface 1602. Equivalently, the rounded housing can, instead of a semi-spherical configuration, be provided in a semi-ovoid configuration, and the flat surface 1602, rather than being circular, can be elliptically shaped or oval shaped. In some embodiments the rounded housing can be semi-spherically configured, and the flat surface 1602 can be elliptical or oval shaped.

Figure 17:
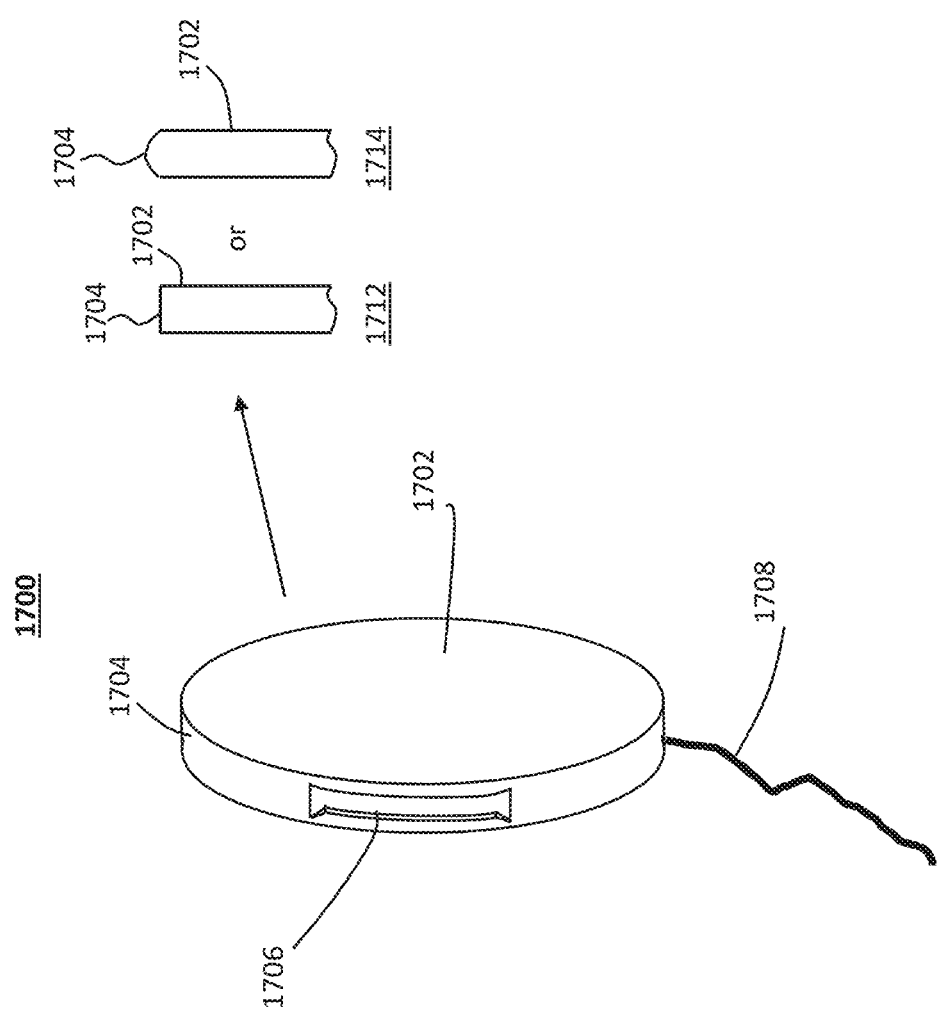
FIG. 17 shows a rounded housing of a digital x-ray sensor device in a disk configuration, in accordance with some embodiments.

FIG. 17 shows a rounded housing 1700 of a digital x-ray sensor device in a disk configuration, in accordance with some embodiments. The rounded housing 1700 here is shaped like a disk, having opposing flat surfaces such as surface 1702, and a wall 1704 around the rounded housing 1700. As shown, the rounded housing is a cylindrical shape having a height that is substantially smaller than its diameter. The flat surfaces (e.g. 1702) can be circular or elliptical or oval. The wall 1704 can be flat in a direction perpendicular to the flat surfaces as shown in side view 1712, or it can be rounded as shown in side view 1714. A handle attachment feature 1706 can be formed on the wall 1704, or on one of the opposite flat surfaces (e.g. 1702). The handle attachment feature 1706 can be formed substantially similar to the handle attachment features shown in FIGS. 6-12. A cable or wire assembly 1708 can carry signals from the digital x-ray sensor housed inside of the rounded housing 1700 to image processing and display equipment.

Figure 18:
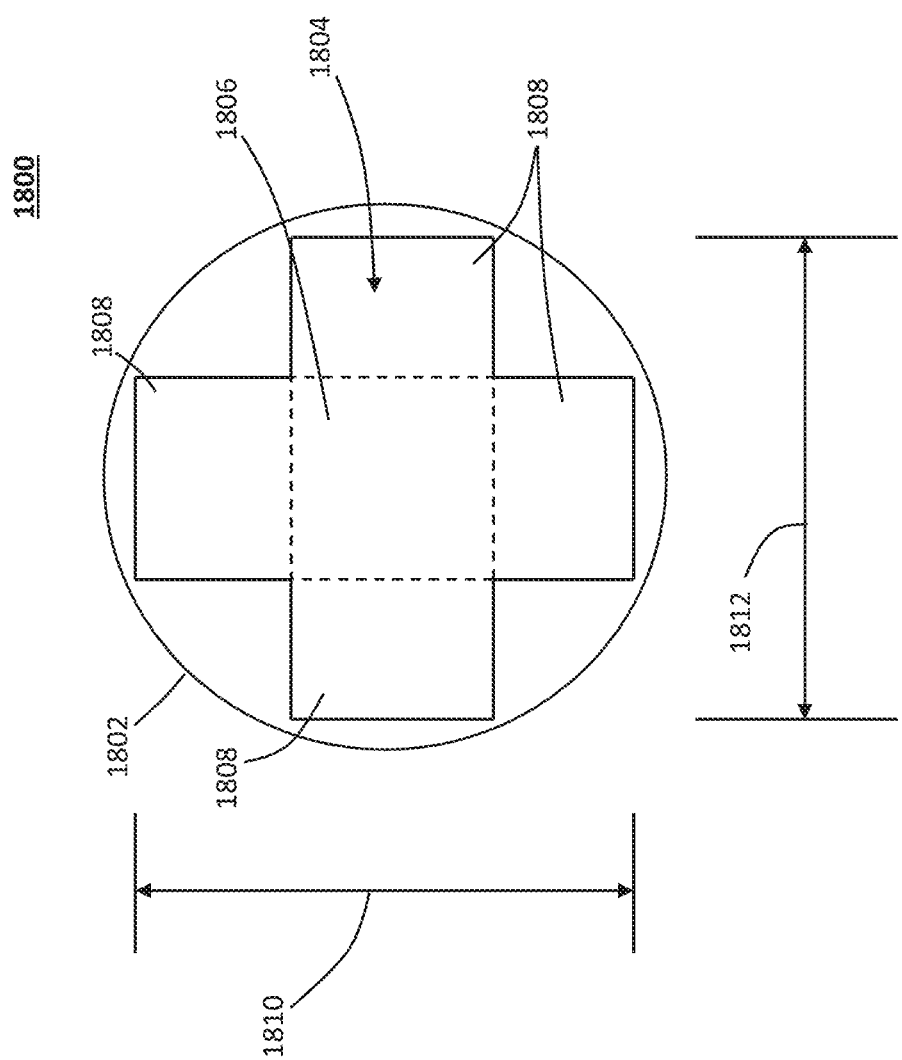
FIG. 18 shows a cross sectional view of a rounded housing having a cross-shaped digital x-ray sensor, in accordance with some embodiments.
Figure 19:
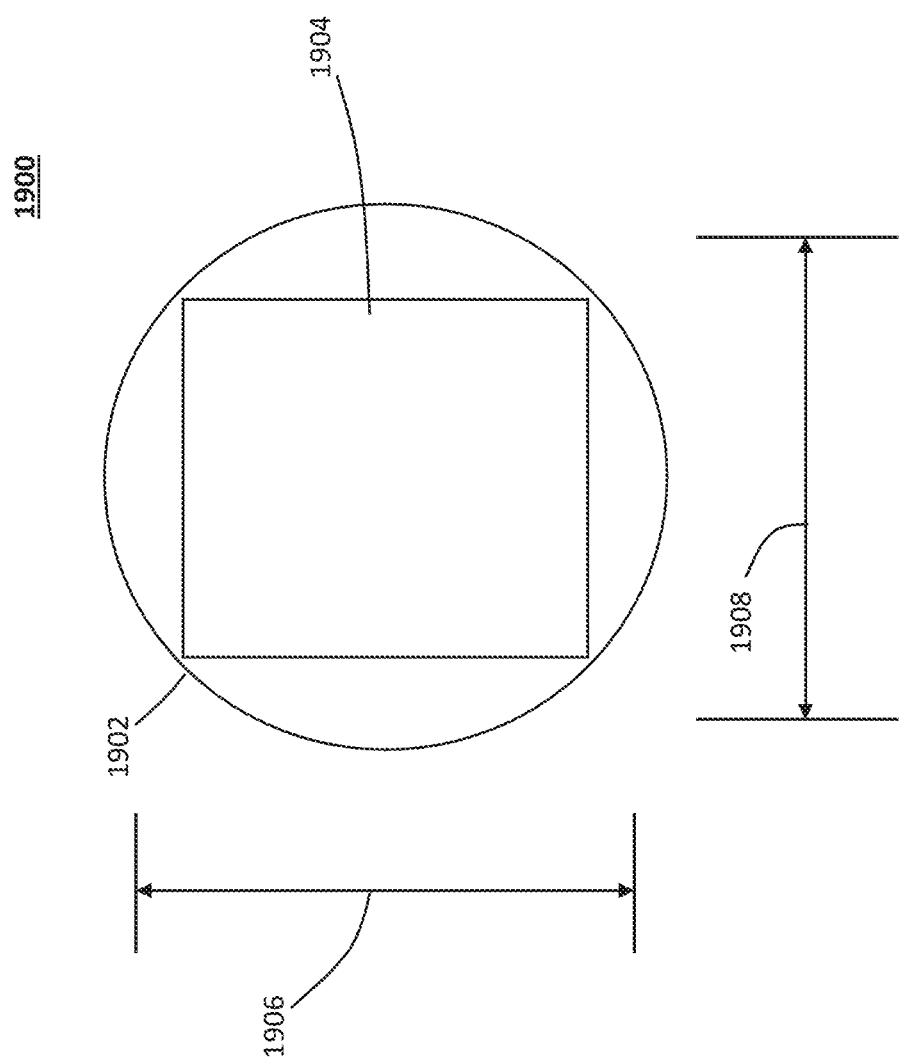
FIG. 19 shows a cross sectional view of a rounded housing having a rectangular-shaped digital x-ray sensor, in accordance with some embodiments.

FIG. 18 shows a cross sectional view of a rounded housing 1800 having a cross-shaped digital x-ray sensor 1804, in accordance with some embodiments. The cross-shaped digital x-ray sensor 1804 can have a central portion 1806 that is square or rectangular, with square or rectangular extensions 1808 at each side of the central portion 1806. The cross-shaped digital x-ray sensor is positioned within rounded housing 1800 within a wall 1802 of the rounded housing 1800, and can be used as an alternative to a circular digital x-ray sensor. Where the wall 1802 can vary in shape from circular, elliptical, or oval, the height 1810 and width 1812 can likewise vary to fit within the wall 1802. FIG. 19 shows a cross sectional view of a rounded housing 1900 having a rectangular-shaped digital x-ray sensor 1904, in accordance with some embodiments. The rectangular-shaped digital x-ray sensor 1904 cane vary in height 1906 and width 1908 with a cross section shape of wall 1902 of the rounded housing 1900. That is, the rounded housing can be spherical, semi-spherical, ellipsoid, or ovoid shaped, and the height 1906 and width 1908 of the rectangular-shaped digital x-ray sensor can be configured accordingly.

A digital x-ray sensor device has been disclosed that houses a digital x-ray sensor in a rounded housing. The rounded housing can be spherically or ellipsoid shaped, generally, but can also include irregular portions so as not to be perfectly spherical or ellipsoid. The rounded housing lacks harsh corners, protrusion, and edges by having a minimum radius for curvature of the external surface of the rounded housing. The minimum radius can be selected to match an average radius of the curvatures of inside the mouths of people. Thus, the rounded housing provides the benefit of comfort when the digital x-ray sensor if placed in the patient's mouth compared to prior art devices that have corners and edges that cause discomfort (or worse). In some embodiments the rounded housing can house a conventional rectangular x-ray sensor, allowing the use of legacy x-ray sensors without the discomfort associated with their use. In some embodiments the rounded housing can house a similarly round or circularly configured x-ray sensor that maximizes the available cross sectional area within the rounded housing for x-ray images. The rounded housing further includes an attachment feature that allows coupling the rounded housing to a handle member for further coupling the digital x-ray sensor to an x-ray source, and ensuring a proper alignment and orientation between the x-ray source and the digital x-ray sensor to produce a particular x-ray image.

What is claimed is:

1. A dental x-ray sensor device, comprising:
    a rounded housing configured to fit in a patient's mouth, and which is further configured to contain a digital x-ray sensor, wherein the rounded housing comprises a flat face that is circular or elliptical that corresponds to a plane of a digital x-ray sensor configured to be mounted in the rounded housing; and
    a handle attachment feature formed on an outside surface of the rounded housing, the handle attachment feature having a plurality of attachment positions.

2. The dental x-ray sensor device of claim 1, wherein the rounded housing comprises a first portion and a second portion that are configured to separably couple together and which comprise a sensor bed that is configured to hold the digital x-ray sensor within the rounded housing.

3. The dental x-ray sensor device of claim 1, wherein the rounded housing is semi-spherically shaped.

4. The dental x-ray sensor device of claim 1, further comprising a circular digital x-ray sensor contained in the rounded housing, and wherein the circular digital x-ray sensor conforms to an internal cross section of the rounded housing.

5. The dental x-ray sensor device of claim 1, wherein the handle attachment feature comprises a groove that is configured to receive a base of a coupling member having detent features, and wherein the groove has a plurality of corresponding detent features at positions along the groove.

6. The dental x-ray sensor device of claim 1, wherein the rounded housing has an external surface having a minimum radius of five millimeters.

7. The dental x-ray sensor device of claim 1, wherein the rounded housing comprises an indicia that indicates an orientation of the digital x-ray sensor inside the rounded housing.

8. A digital dental x-ray sensor device, comprising:
    a rounded housing having an external surface, the rounded housing being configured to fit within a person's mouth with the person's mouth substantially closed, wherein the rounded housing comprises a flat face that is circular or elliptical that corresponds to a plane of an image sensor configured to be mounted in the rounded housing;
    a digital x-ray sensor disposed within the rounded housing that conforms to an internal cross section of the rounded housing; and
    an attachment feature including a channel on an exterior of the rounded housing that is configured to receive a coupling member in the channel.

9. The digital dental x-ray sensor device of claim 8, wherein the rounded housing is a spherical housing.

10. The digital dental x-ray sensor device of claim 9, wherein the spherical housing is a sphere having at least one flat portion.

11. The digital dental x-ray sensor device of claim 8, wherein the rounded housing is an ellipsoid.

12. The digital dental x-ray sensor device of claim of claim 8, wherein the rounded housing comprises at least one flat spot.

13. The digital dental x-ray sensor device of claim 8, wherein the digital x-ray sensor has a circular shape.

14. The digital dental x-ray sensor device of claim 8, wherein the attachment feature is positioned on the rounded housing in front of the digital x-ray sensor.

15. The digital dental x-ray sensor device of claim 8, wherein the attachment feature comprises a plurality of detent features, each one of the plurality of detent features corresponding to a respective position along the channel and configured to mate with a corresponding detent feature on the coupling member.

16. A digital dental x-ray sensor system, comprising:
    a digital dental x-ray sensor device having a rounded housing, a digital x-ray sensor disposed within the rounded housing, and an attachment feature including a channel formed on an exterior of the rounded housing, wherein the rounded housing comprises a flat face that is circular or elliptical that corresponds to a plane of an image sensor configured to be mounted in the rounded housing;
    a coupling member having a portion configured to fit within the channel and be moveably retained in the channel, and having a head portion connected to the portion of the coupling member configured to fit within the channel;

a handle member having a first end configured to attach to the head portion of the coupling member, and having a second end opposite the first end; and a coupling ring including a track configured to be retained on an emitter portion of an x-ray source, and having an extension that extends from the track formed on the coupling ring that is configured to attach to the second end of the handle member.

17. The digital dental x-ray sensor system of claim 16, wherein the rounded housing is spherical.

18. The digital dental x-ray sensor system of claim 16, wherein the digital dental x-ray sensor device is semi-spherical.

19. The digital dental x-ray sensor system of claim 16, wherein:

the channel of the attachment feature comprises a plurality of detent features, where each one of the plurality of detent features corresponds to a respective one of a plurality of positions along the channel; and the portion of the coupling member configured to fit with the channel includes corresponding detent features to mate with the plurality of detent features in the channel to hold the coupling member at one of the plurality of positions along the channel.

20. The digital dental x-ray sensor system of claim 16, wherein the extension of the coupling ring is movable along the track to hold the extension at a selected position along the track.

* * * * *